United States Patent [19]

Takase et al.

[11] Patent Number: 5,055,588
[45] Date of Patent: Oct. 8, 1991

[54] PROCESS FOR PREPARING N-SUBSTITUTED AMINO ACID ESTERS

[75] Inventors: Ichirou Takase; Kazuo Sato; Noritsugu Yamasaki; Yukihisa Goto, all of Himeji, Japan

[73] Assignee: Daicel Chemical Industries Ltd., Japan

[21] Appl. No.: 520,961

[22] Filed: May 9, 1990

Related U.S. Application Data

[63] Continuation of Ser. No. 215,609, Jul. 6, 1988, abandoned.

[51] Int. Cl.$^5$ .......................................... C07D 233/64
[52] U.S. Cl. ..................................... 548/344; 560/34; 560/38; 560/39; 560/40; 560/155; 560/168; 560/169; 560/173
[58] Field of Search .................. 560/38, 34, 39, 40, 560/155, 168, 169, 173; 548/344

[56] References Cited

U.S. PATENT DOCUMENTS

| | | | |
|---|---|---|---|
| 4,344,949 | 8/1982 | Hoefle et al. | 424/258 |
| 4,350,704 | 9/1982 | Hoefle et al. | 424/274 |
| 4,542,234 | 9/1985 | Reilly, Jr. et al. | 560/38 |
| 4,596,791 | 6/1986 | Piwinski et al. | 574/19 |

FOREIGN PATENT DOCUMENTS

| | | |
|---|---|---|
| 0049605 | 4/1982 | European Pat. Off. . |
| 3303344 | 8/1984 | Fed. Rep. of Germany . |
| 59-17244 | 2/1984 | Japan . |
| 60-13715 | 1/1985 | Japan . |

*Primary Examiner*—Bruce Gray
*Attorney, Agent, or Firm*—Bryan, Cave, McPheeters & McRoberts

[57] ABSTRACT

A process for preparing N-substituted amino acid esters having the formula (I):

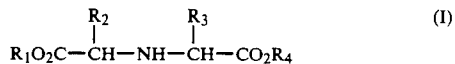

(I)

wherein $R_1$ and $R_4$, the same or different, are an alkyl, aralkyl, cycloalkyl or aryl group; and $R_2$ and $R_3$, the same or different, are an alkyl, aralkyl, aryl, heterocyclealkyl, aminoalkyl or guanidylalkyl, by the reaction of α-amino acid esters with α-substituted carboxylic acid esters, under the condition of substantially free from solvent, which can afford their optical isomers in a good yield.

10 Claims, No Drawings

PROCESS FOR PREPARING N-SUBSTITUTED AMINO ACID ESTERS

This is a continuation of U.S. application Ser. No. 07/215,609, filed July 6, 1988 now abandoned.

BACKGROUND OF THE INVENTION

1. Field of the Invention

This invention relates to a process for preparing N-substituted amino acid esters. More particularly, it relates to an asymmetric synthetic method for preparing N-substituted α-amino acids from α-amino acid esters and α-substituted carboxylic acid esters.

2. Description of the Prior Art

Some N-substituted amino acid esters are useful as intermediates for the synthesis of various amino acid derivatives which show inhibitory action on angiotensin-transformation enzyme and hence can be used as antidepressants and also are useful as various physiologically active substances such as amavadin, histopine and octopine of natural origins.

(S,S)-N-substituted amino acid esters have been prepared e.g., by reacting (S)-α-amino acid esters with an equimolar amount of α-halocarboxylic acid esters in the presence of sodium carbonate and in an organic solvent such as dimethyl formamide. The yields however were not satisfactory, in the order of e.g., 46%, based upon theoretical yield of (S,S)-diastereoisomer (see U.S. Pat. No. 4,542,234). Similarly, methods to conduct these syntheses in organic solvents are also known [see U.S. Pat. No. 4,344,949, U.S. Pat. No. 4,596,791 and Japanese Unexamined Patent Publication No. Sho 60(1985)-13715].

N-Substituted amino acid esters also have been prepared by the reaction of amino acid esters with trifluoro-methyl-sulfonyloxy substituted carboxylic acid esters in the presence of triethylamine and in an organic solvent such as methylene chloride, with high yield (see DE 3,303,344, Japanese Unexamined Patent Publication No. Sho 59(1984)-172442).

It has been reported that in the preparation of N-substituted amino acid esters from amino acid esters and α-halo carboxylic esters, α-tosyloxy carboxylic acid esters or α-mesyloxy carboxylic acid esters, silber ion catalyst was required to achieve high yield (see U.S. Pat. No. 4,350,704).

In such known methods, all the reactions are conducted in a homogeneous system using organic solvents and do not afford a sufficient yield unless carboxylic acid esters having very strong active trifluorosulfonyloxy group or silber ion catalyst are used. Furthermore carboxylic acid esters having trifluorosulfonyloxy group must be handled with due attention because they are unstable and show a tearing property. Accordingly, it is desired to develop a method for the preparation of N-substituted amino acid esters in high yield which can be easily treated and conducted under conditions which are not severe.

Thus, the inventors have found an efficient asymmetric synthetic method for preparing N-substituted amino acid esters which is conducted in the absence of solvent and affords a good yield.

SUMMARY OF THE INVENTION

This invention provides a process for preparing a N-substituted amino acid ester having the formula (I):

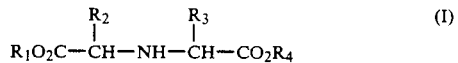

wherein $R_1$ and $R_4$ may be the same or different and are an alkyl, aralkyl, cycloalkyl or aryl group; and $R_2$ and $R_3$ may be the same or different and are an alkyl, aralkyl, aryl, heterocyclicalkyl, aminoalkyl or guanidylalkyl, which comprises reacting an α-amino acid ester of the formula (II):

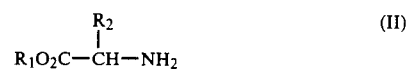

wherein the symbols have the same meaning as defined in formula (I), with an α-substituted carboxylic acid ester of the formula (III):

wherein X is a leaving group and $R_3$ and $R_4$ have the same meaning as defined in formula (I), in the presence or absence of a base under the condition of substantially free from solvent, while heating and isolating the product resultant (I).

In $R_1$ and $R_4$ of formula (I), the alkyl group means a straight chain or branched chain alkyl having one to six carbon atoms such as methyl, ethyl, propyl, isopropyl, n-butyl, iso-butyl, sec-butyl or tert-butyl. Examples of the aralkyl groups are benzyl, α-phenethyl, β-phenethyl, 4-hydroxybenzyl or 3,4-dihydroxybenzyl. Examples of the cycloalkyl groups are cyclopentyl, cyclohexyl or cycloheptyl. Examples of the aryl groups are phenyl or phenyl substituted by an alkyl, a halogen, nitro or hydroxy.

In $R_2$ and $R_3$ of formula (I) the alkyl, aralkyl and aryl groups may be the same ones as mentioned in $R_1$ and $R_2$. The heterocyclic-substituted alkyl group may be imidazolylmethyl, the aminoalkyl group may be 4-aminobutylbutyl, and the guanidylalkyl may be guanidylmethyl or guanidylethyl.

$R_1$, $R_2$, $R_3$ and $R_4$ of formulas (II) and (III) have the same meaning as defined in formula (I).

The leaving group X of formula (III) may be a halogen atom such as chlorine, bromine and iodine; an aliphatic sulfonyloxy group such as methane sulfonyloxy, ethane sulfonyloxy or butane sulfonyloxy; an aromatic sulfonyloxy group such as benzene sulfonyloxy, p-toluene sulfonyloxy, p-bromobenzene sufonyloxy or p-nitrobenzene sulfonyloxy; and a halo sulfonyloxy such as chlorosulfonyloxy.

The object compound of formula (I) includes (S,S)- and (R,R)-configurations as absolute structure thereof. For this purpose, the starting materials, i.e., the compound of formula (II) as well as the compound of formula (III), are those having the (S) or (R)-configuration. Especially, in accordance with the process of this invention, (S,S)-compound of the formula (I) can be obtained in a good yield, when (S)-compound of the formula (II) and (R)-compound of the formula (III) are used. Similarly, (R,S)-compound, (S,R)-compound and (R,R)-compound of the formula (I) may be obtained from (R)-compound (II) and (R)-compound (III), (S)- compound (II) and (S)-compound (III), and (R)-compound (II) and (S)-compound (III), respectively.

The starting materials, the compounds of formula (II) or (III) are partially known and can be easily prepared from known compounds in accordance with conventional methods. For example, compound (II) can be prepared by esterifying an appropriate alcohol with an amino acid such as alanine, phenylalanine, tyrosine, homophenylalanine, valine, lysine, arginine, histidine, phenylglycine, 4-hydroxyphenyl glycine or dopa [3-(3,4-dihydroxyphenyl)alanine]. Also, compound (III) can be prepared e.g., diazotizing an amino acid followed by halogenating, hydrating or sulfonating, or by asymmetrically reducing an α-keto acid, followed by halogenation or sulfonation.

The amino acids as mentioned above are, preferably optically active ones having the (R) or (S)-configuration but when the racemates are used, the products are also optically active.

In the process of this invention, compound (II) is reacted with compound (III) under the condition of substantially free from solvent.

The wording "substantially free from solvent" means that any solvent is not positively or intentionally added or employed. However, the reaction system may contain an organic solvent included in the starting material employed which comes from its manufacturing process, e.g., in an extent of 5 or like % of the starting material.

It is found that the yield of the reaction when conducted in the absence of solvent in accordance with this invention is significantly improved in comparison with that of the reaction in the presence of organic solvent, although it may be influenced by the kinds and ratios of the starting materials.

It is preferred to use either compound (II) or compound (III) in an excess amount, e.g., 1.1 or more mols. It is especially preferred to use two or more molar amounts of the compound (II) to one mole of the compound (III). In this case, the reaction can be conduct without addition of a base to neutralize acidic substances formed by the reaction since compound (II) existing in excess can act as a base. When the compound (II) is used in excess, it is easily recovered after the reaction and can be reused in another batch of the reaction. However, it is not generally recommended from the industrial viewpoint to use more than four molar amounts of the compound (III), because it is rather expensive.

The reaction of this invention may be carried out in the presence of a base. The base is usually used in an amount nearly equal to the lesser amount of either compound (II) or (III). However, when the base is potassium or sodium carbonate which may make the reaction system to heterogeneous one, it is desirably used in 1.0 or 2.0 equal amount to a lesser amount of either the compound (II) or (III).

Examples of the bases include organic bases such as triethylamine, trioctylamine, pyridine, N,N-dimethylaminopyridine and diazabicycloundecene, or inorganic bases such as sodium carbonate, potassium carbonate, lithium carbonate and magnesium carbonate as well as their corresponding hydrogen carbonates. It is preferable to use sodium carbonate or potassium carbonate, although they are insoluble in any of the compounds of the formula (II) and (III), because they provide a higher yield of the object compound (I) than the organic bases.

The reaction is generally conducted between a slightly elevated temperature and a temperature which does not cause decomposition of the raw materials, preferably between 50° C.–130° C., more preferably between 70° C.–110° C. The reaction will be generally completed in several hours to a day. It is preferred to apply efficient stirring for the reaction mixture.

After completing the reaction, the object compound (I) may be isolated e.g., by adding water and ethyl ether to the reaction mixture, collecting the ether layer, removing the solvent, dissolving the oily residue in a mixture of methylene chloride and ethyl acetate (20 : 1) and subjecting the solution to silica gel-chromatography. Other conventional methods can also be utilized to isolate the object compound.

This invention is further illustrated by examples.

EXAMPLE 1

Preparation of benzyl N-[(1S)-1-ethoxycarbonyl-3-phenylpropyl]-L-alanate (I-a)

Ethyl (S)-homophenylalanate (0.415 g, 2.00 mmol), benzyl (R)-α-toluenesulfonyloxypropionate (0.661 g, 2.00 mmol) and potassium carbonate (0.207 g, 1.50 mmol) were added into a two-necked flask equipped with a condenser and a thermometer, and stirred for 6 hours at 70° C. After completing the reaction, the mixture was gradually cooled to 60° C., to which toluene (10 ml) was added in order to prevent hardening. At the stage that the mixture was cooled to room temperature, water was added to the mixture to dissolve an insoluble salt. Then, the mixture was extracted with toluene twice. The combined toluene layers were dried over magnesium sulfate, filtered and concentrated under reduced pressure. The obtained pale yellow oil was subjected to column-chromatography on silica gel eluting with methylene chloride-ethyl acetate [20 : 1 (v/v)]to give 0.608 g (1.65 mmol, 82.3%) of the title compound (I-a). Its physical properties are as follows.

$[\alpha]^{25}_D = -18.4°$ (c=1, CHCl3)

$^1$H-NMR(δ,ppm) : 1.23(t,J=7Hz,3H), 1.31(d,J=7Hz,3H), 1.80(br,1H), 1.70–2.19(m,2H), 2.55–2.82(m,2H), 3.20–3.46(m,2H), 4.12 (q,J=7Hz,2H), 5.08(s,2H), 7.12 (s,5H), 7.26(s,5H)

IR(cm$^{-1}$) : 1740 (C=O)

MS(m/z) : 369(M+), 296(M+—$CO_2$Et), 234 (M+—$CO_2CH_2$Ph)

(S,S)-compound : (R,R)-compound : diastereomer (S,R+R,S)= 98.4 : 0 : 1.6 (by HPLC using column for optical resolution)

EXAMPLES 2–15

In a manner similiar to Example 1, ethyl(S)-homophenylalanate [II; $R_1$=Et, $R_2$=Ph(CH$_2$)$_2$] and benzyl (R)-α-toluenesulfonyloxypropionate [III, $R_3$=Me, $R_4$=Ph(CH$_2$)$_2$] in the presence or absence of a base were reacted under the conditions mentioned in Table 1. The reaction mixture was treated in a manner similar to Example 1 to give benzyl N-[(1S)-1-ethoxycarbonyl-3-phenylpropyl]-L-alanate (I-a).

TABLE 1

| Example No. | Ratio in Mol. of the raw materials (II) | (III) | base | Reaction Temp. (°C.) | Reaction Time (hr.) | Yield (%) on (S,S)-isomer | Ratio of isomers (S,S):(R,R):diastereoisomer | Optical* rotation (°) |
|---|---|---|---|---|---|---|---|---|
| 2 | 6 | 2 | — | 90 | 3.0 | 87.7 | 98.8:0:1.2 | −18.9 |
| 3 | 6 | 2 | — | 90 | 6.0 | 89.2 | 98.8:0:1.2 | −18.9 |
| 4 | 4 | 2 | — | 90 | 6.0 | 87.9 | 98.7:0:1.3 | −18.5 |
| 5 | 2.2 | 2 | $K_2CO_3$ 1.0 | 80 | 12 | 82.5 | 97.8:0:2.2 | −17.8 |
| 6 | 2.2 | 2 | $K_2CO_3$ 1.0 | 60 | 24 | 79.5 | 98.9:0:1.1 | −17.0 |
| 7 | 2 | 2 | $K_2CO_3$ 1.0 | 90 | 6.0 | 69.8 | 98.9:0:1.2 | −18.4 |
| 8 | 2 | 2 | $K_2CO_3$ 1.0 | 80 | 12 | 77.5 | 97.8:0:2.2 | −17.8 |
| 9 | 2 | 2 | $K_2CO_3$ 1.0 | 60 | 24 | 61.2 | 98.9:0:1.1 | −17.0 |
| 10 | 2 | 2 | $K_2CO_3$ 1.5 | 80 | 6.0 | 64.9 | 99.0:0:1.0 | −18.4 |
| 11 | 2 | 3 | $K_2CO_3$ 1.5 | 90 | 3.0 | 81.4 | 98.2:0:1.8 | −18.4 |
| 12 | 2 | 4 | $K_2CO_3$ 1.5 | 90 | 3.0 | 86.5 | 98.9:0:1.1 | −18.7 |
| 13 | 2 | 6 | $K_2CO_3$ 1.5 | 90 | 3.0 | 88.2 | 99.0:0:1.0 | −18.6 |
| 14 | 2 | 2 | MgO 1.0 | 90 | 6.0 | 70.7 | 95.7:0:4.3 | −18.1 |
| 15 | 2 | 2 | $Et_3N$ 3.0 | 90 | 3.0 | 90.0 | 90.3:0.55:9.2 | −16.1 |

*$[\alpha]_D^{25}$ (C = 1, $CHCl_3$)

EXAMPLES 16–25

Instead of ethyl (S)-homophenylalanate and benzyl (R)-α-toluenesulfonyloxypropionate used in Example 1, other (S)-amino acid esters (II) and (R)-carboxylic acid esters (III) were reacted and subjected to after-treatment in the same way as Example 1. The reactants and the conditions of these reactions are shown in Table 2.

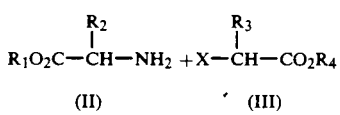

(II)      (III)

-continued

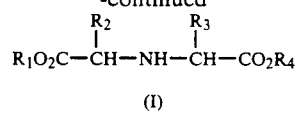

(I)

TABLE 2

| Example No. | (II) R₁ | R₂ | (III) R₃ | R₄ | X | Ratio in Mol. (II) | (III) | base | (I) | yield (%) | Optical rotation [α]_D(°) |
|---|---|---|---|---|---|---|---|---|---|---|---|
| 16 | Et | Me | Me | Me | OTs | 9 | 3 | — | I-b | 89.3 | −42.4 |
| 17 | Et | Me | Me | Me | OTs | 2 | 4 | $K_2CO_3$ 1.5 | I-b | 85.4 | −42.0 |
| 18 | Et | $PhCH_2$ | Me | Me | OTs | 2 | 4 | $K_2CO_3$ 1.5 | I-c | 87.1 | |
| 19 | Et | $Ph(CH_2)_2$ | Me | $PhCH_2$ | OMs | 9 | 3 | — | I-a | 89.6 | −18.9 |
| 20 | Et | $Ph(CH_2)_2$ | Me | $PhCH_2$ | OMs | 2 | 3 | $K_2CO_3$ 1.5 | I-a | 83.7 | −18.4 |
| 21 | Et | $Ph(CH_2)_2$ | Me | Me | OTs | 10 | 10 | $K_2CO_3$ 7.5 | I-d | 74.9 | −14.9 |
| 22 | Et | $Ph(CH_2)_2$ | Me | Et | OTs | 10 | 10 | $K_2CO_3$ 7.5 | I-e | 80.9 | −12.7 |
| 23 | $PhCH_2$ | $Ph(CH_2)_2$ | Me | $PhCH_2$ | OTs | 6.4 | 6.4 | $K_2CO_3$ 4.8 | I-f | 74.7 | |
| 24 | $PhCH_2$ | $Ph(CH_2)_2$ | Me | Me | OTs | 7.4 | 8.1 | $K_2CO_3$ 11.2 | I-g | 64.8 | |
| 25 | $PhCH_2$ | $Ph(CH_2)_2$ | Me | Et | OTs | 5 | 5 | $K_2CO_3$ 3.75 | I-h | 71.6 | −22.2 |

The physical properties of the compounds obtained in Examples 16–25 are as follows:

[I-b] methyl N-[(1S)-1-ethoxycarbonylethyl]-L-alanate
$C_9H_{17}NO_4 = 203.24$
$[\alpha]^{28}_D = -42.4°$ ($CHCl_3$, c = 0.86)
¹H-NMR(δ,ppm): 1.28(t,J=7Hz,3H), 1.33(d,J=7Hz,3H), 1.34(d,J=7Hz,3H), 2.23(s,1H), 3.40(q,J=7Hz,1H), 3.42(q,J=7Hz,1H), 3.73(s,3H), 4.18(q,J=7Hz,2H)

[I-c] methyl N-[(1S)-1-ethoxycarbonyl-2-phenylethyl]-L-alanate
$C_{15}H_{21}NO_4 = 279.34$ $^1$H-NMR($\delta$, ppm) : 1.17(t,J=7Hz,3H), 1.27(d,J=7Hz,3H), 1.93(s,1H), 2.87-2.95(m,2H), 3.20-3.47(m,2H), 3.60(s,3H), 4.10 (q,J=7Hz,2H), 7.17(s,5H)

[I-d] methyl N-[(1S)-1-ethoxycarbonyl-3-phenylpropyl]-L-alanate $C_{16}H_{23}NO_4 = 293.36$ $[\alpha]^{31}_D = -14.9°$ (c=1.0, CHCl$_3$)
$^1$H-NMR($\delta$,ppm) : 1.27(t,7Hz,3H), 1.32(d,J=7Hz,3H), 1.83(s,1H), 1.70-2.13(m,2H), 2.58-2.83(m,2H), 3.30(t,J=7Hz,1H), 3.35(q,J=7Hz,1H), 3.67(s,3H), 4.12(q,J=7Hz,2H), 7.15(s,5H)

[I-e] ethyl N-[(1S)-1-ethoxycarbonyl-3-phenylpropyl]-L-alanate $C_{17}H_{25}NO_4 = 307.39$
$[\alpha]^{31}_D = -12.7°$ (c=1.2, CHCl$_3$)
$^1$H-NMR($\delta$,ppm) : 1.27(t,J=7Hz,3H), 1.30(t,J=7Hz,3H), 1.35(d,J=7Hz,3H), 1.83(s,1H), 1.75-2.10(m,2H), 2.60-2.85(m,2H), 3.30(t,J=7Hz,1H), 3.33(q,J=7Hz,1H), 4.13(q,J=7Hz,2H), 4.17(q,J=7Hz,2H), 7.20(s,5H)

[I-f] benzyl N-[(1S)-1-benzyloxycarbonyl-3-phenylpropyl]-L-alanate $C_{27}H_{29}NO_4 = 431.53$
$^1$H-NMR($\delta$,ppm) : 1.30(d,J=7Hz,3H), 1.77(s,1H), 1.67-2.00(m,2H), 2.50-2.77 (m,2H), 3.37(t,J=7Hz,1H), 3.40(q,J=7Hz,1H), 5.05(s,4H), 7.07(s,5H), 7.23(s,10H)

[I-g] methyl N-[(1S)-1-benzyloxycarbonyl-3-phenylpropyl]-L-alanate $C_{21}H_{25}NO_4 = 355.43$
$^1$H-NMR($\delta$,ppm) : 1.32(d,J=7Hz,3H), 1.87(s,1H), 1.73-2.10(m,2H), 2.53-2.80(m,2H), 3.36(q,J=7Hz,1H). 3.37(t,J=7Hz,1H), 3.67(s,3H), 5.13(s,2H), 7.15(s,5H), 7.30(s,5H)

[I-h] ethyl N-[(1S)-1-benzyloxycarbonyl-3-phenylpropyl]-L-alanate $C_{22}H_{27}HO_4 = 369.46$
$[\alpha]^{24}_D = -22.24°$ (c=1.0, CHCl$_3$)
$^1$N-NMR($\delta$,ppm) : 1.23(t,J=7Hz,3H), 1.28(d,J=7Hz,3H), 1.80(s,1H), 1.73-2.10(m,2H), 2.53-2.79(m,2H), 3.33(q,J=7Hz,1H), 3.39 (t,J=7Hz,1H), 4.10(q,J=7Hz,2H), 5.07(s,2H), 7.07(s,5H), 7.23(s,5H)

COMPARATIVE EXAMPLES 1-3 (U.S. Pat. No. 4,542,234)

Ethyl (S)-homophenylalanine (I') and benzyl (R)-α-toluenesulfonyloxypropionate (II') in the presence or absence of potassium carbonate were added to acetonitrile (15 ml, bp 82° C.), and refluxed for a predetermined time, while stirring. After completing the reaction, the mixture was concentrated under reduced pressure and water (10 ml) was added to the oily residue. Then the mixture was extracted with toluene (10 ml). The organic layer was concentrated under reduced pressure to remove toluene. The oily residue was subjected to silica gel column chromatography to give the compound N-[(1S)-1-ethoxycarbonyl-3-phenylpropyl]-L-alanine. The reaction conditions are shown in Table 3.

TABLE 3

| Comparative Example No. | Ratio in Mol. | | | Reaction Time (hr.) | Yield of (S,S)isomer | Ratio of Optical Isomer (S:S):(R:R):diastereoisomer |
|---|---|---|---|---|---|---|
| | (I') | (II') | K$_2$CO$_3$ | | | |
| 2 | 2.0 | 3.0 | 1.0 | 6 | 30.9 | 99.0:0:1.0 |
| 3 | 4 | 2 | — | 12 | 42.5 | 99.0:0:1.0 |
| 4 | 8 | 2 | — | 12 | 69.0 | 99.0:0:1.0 |

What is claimed is:

1. A process for preparing an optically active N-substituted amino acid ester having the formula (I);

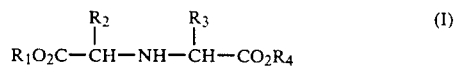

wherein R$_1$ and R$_4$ may be the same or different and are an alkyl, aralkyl, cycloalkyl or aryl group; and R$_2$ and R$_3$ may be the same or different and are an alkyl, aralkyl, aryl, heterocyclicalkyl, aminoalkyl or guanidylalkyl group, which comprises reacting at an elevated termperature an optically active alpha-amino acid ester of the formula (II);

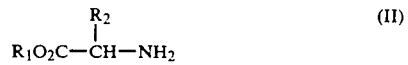

wherein R$_1$ and R$_2$ have the same meaning as defined in formula (I), with an optically active alpha-substituted carboxylic acid ester of the formula (III);

wherein X is an aliphatic or aromatic sulfonyloxy group and R$_3$ and R$_4$ have the same meaning as defined in formula (I), in the presence or absence of a base and in the presence of 5% or less, based on the starting materials, of a solvent, to invert the optical configuration at the alpha position of substantially all of the carboxylic acid ester of the formula (III) and subsequently isolating the resultant optically active produce (I).

2. A process of claim 1 in which the reaction is conducted at a temperature between a slightly elevated temperature to a temperature for not causing decomposition of the compound (II) or (III) to be employed.

3. A process of claim 2 in which the reaction temperature is in the range of 50° C. to 130° C.

4. A process of claim 2 in which the reaction temperature is in the range of 70° C. to 110° C.

5. A process of claim 1 in which the base in used and either the compound (II) or the compound (III) is used in an equimolar or more amount.

6. A process of claim 5 in which the compound (II) is used in two to four molar amounts to one mol of the compound (III).

7. A process of claim 1 in which the base is used in an equivalent or more amount to either one of the compound (II) or the compound (III) which is used in a lesser amount between them.

8. A process of claim 7 in which the base is potassium carbonate.

9. A process of claim 1 which is adopted to prepare (S,S)-compound (I) from (S)-compound (II) and (R)-compound (III).

10. A process of claim 1 which is adopted to prepare (R,R)-compound (I) from (R)-compound (II) and (R)-compound (III).

* * * * *

UNITED STATES PATENT AND TRADEMARK OFFICE
CERTIFICATE OF CORRECTION

PATENT NO. : 5,055,588
DATED : October 8, 1991
INVENTOR(S) : ICHIROU TAKASE et al.

It is certified that error appears in the above-identified patent and that said Letters Patent is hereby corrected as shown below:

In the Abstract: Change "heterocycle-alkyl" to --heterocyclicalkyl--.

Column 1, line 29: Change "diasteroisomer" to --diastereoisomer--.

Column 1, line 36: Delete "also".

Column 2, lines 28-29: Change "product resultant" to --resultant product--.

Column 2, line 30: Change "means" to --is--.

Column 2, line 54: Change "sufonyloxy" to --sulfonyloxy--.

Column 3, line 12: Change "diazotizing" to --by diazotizing--.

Column 3, line 38: Change "mols." to --moles.--.

Column 3, line 41: Change "conduct" to --conducted--.

Column 4, line 47: Change "CHC13" to --$CHCl_3$--.

Column 4, line 55: Change "diastereomer" to --diastereoisomer--.

Column 7, line 1: Change "($\delta$,      ppm)" to --($\delta$,ppm)--.

Column 7, line 3: Change "4.10    (q,J=7Hz,2H)" to --4.10(q,J=7Hz,2H)--.

UNITED STATES PATENT AND TRADEMARK OFFICE
CERTIFICATE OF CORRECTION

PATENT NO. : 5,055,588

DATED : October 8, 1991

INVENTOR(S) : ICHIROU TAKASE et al.

It is certified that error appears in the above-identified patent and that said Letters Patent is hereby corrected as shown below:

Column 7, line 54: Change "$C_{22}H_{27}HO_4=369.46$" to --$C_{22}H_{27}NO_4=369.46$--.

Column 8, line 63: In claim 5, change "in used" to --is used--.

Column 8, line 67: In claim 6, change "mol" to --mole--.

Signed and Sealed this

Twenty-third Day of March, 1993

Attest:

STEPHEN G. KUNIN

*Attesting Officer*         *Acting Commissioner of Patents and Trademarks*